US008058412B2

(12) United States Patent
Ishii et al.

(10) Patent No.: US 8,058,412 B2
(45) Date of Patent: Nov. 15, 2011

(54) DEHYDROXYFLUORINATION AGENT

(75) Inventors: Akihiro Ishii, Saitama (JP); Takashi Ootsuka, Fujimino (JP); Manabu Yasumoto, Fujimino (JP); Hideyuki Tsuruta, Fujimino (JP); Kenjin Inomiya, Fujimino (JP); Koji Ueda, Fujimino (JP); Kaori Mogi, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/306,826

(22) PCT Filed: Jun. 25, 2007

(86) PCT No.: PCT/JP2007/062687
§ 371 (c)(1),
(2), (4) Date: Dec. 29, 2008

(87) PCT Pub. No.: WO2008/001718
PCT Pub. Date: Jan. 3, 2008

(65) Prior Publication Data
US 2009/0250658 A1 Oct. 8, 2009

(30) Foreign Application Priority Data
Jun. 30, 2006 (JP) ................. 2006-182235

(51) Int. Cl.
C07D 478/00 (2006.01)
C09K 3/00 (2006.01)
C07C 17/00 (2006.01)
C07C 19/08 (2006.01)
C07C 21/18 (2006.01)

(52) U.S. Cl. ....... 532/1; 252/182.32; 570/123; 570/124; 570/126

(58) Field of Classification Search ............. 252/182.12; 560/111, 103, 227; 570/140, 165, 127, 123–124, 570/126; 562/852, 307; 532/1
See application file for complete search history.

(56) References Cited

U.S. PATENT DOCUMENTS

| | | | |
|---|---|---|---|
| 5,760,255 A | 6/1998 | Vorbruggen et al. | |
| 6,248,889 B1 | 6/2001 | Savu et al. | |
| 6,723,874 B1 * | 4/2004 | Braun et al. | 562/852 |
| 7,388,094 B2 | 6/2008 | Ishii et al. | |
| 7,462,734 B2 | 12/2008 | Ishii et al. | |
| 2004/0097758 A1 * | 5/2004 | Braun et al. | 562/849 |
| 2008/0103327 A1 | 5/2008 | Ishii et al. | |
| 2008/0125589 A1 | 5/2008 | Ishii et al. | |

FOREIGN PATENT DOCUMENTS

| | | |
|---|---|---|
| JP | 9-507503 A | 7/1997 |
| JP | 2002-531426 A | 9/2002 |
| JP | 2005-126386 A | 5/2005 |
| JP | 2005-336151 A | 12/2005 |
| JP | 2006-8534 A | 1/2006 |
| JP | 2006-83163 A | 3/2006 |
| JP | 2006-290870 | * 10/2006 |
| JP | 2006-290870 A | 10/2006 |

OTHER PUBLICATIONS

Jingjun Yin, et al., "Direct and Convenient Conversion of Alcohols to Fluorides", American Chemical Society, Organics Letters, (US) 2004, vol. 6 No. 9, p. 1465-1468.
T.S. Chou, et al., "Triethylamine Poly(Hydrogen Fluorides) in the Synthesis of a Fluorinated Nucleoside Glycon", Pergamon, Tetrabedron, Letters, (UK) 1996, vol. 37, No. 1, p. 17-20.
Peter J. Stang, et al., "Perfluoroalkanesulfonic Esters: Methods of Perparation and Applications in Organic Chemistry", Synthesis (Germany) 1982, vol. 2, p. 85-126.
International Search Report dated Jul. 31, 2007 including English translation of the relevant portion (Fourteen (14) pages).

* cited by examiner

Primary Examiner — Ling Choi
Assistant Examiner — Monique Peets
(74) Attorney, Agent, or Firm — Crowell & Moring LLP

(57) ABSTRACT

There is provided a novel, useful dehydroxyfluorination agent containing sulfuryl fluoride ($SO_2F_2$) and an organic base that is free from a free hydroxyl group in the molecule. According to the present dehydroxyfluorination agent, it is not necessary to use perfluoroalkanesulfonyl fluoride, which is not preferable in large-scale use, and it is possible to advantageously produce optically-active fluoro derivatives, which are important intermediates of medicines, agricultural chemicals and optical materials, for example, 4-fluoroproline derivatives, 2'-deoxy-2'-fluorouridine derivatives, optically-active α-fluorocarboxylate derivatives, and monofluoromethyl derivatives, even in large scale.

8 Claims, No Drawings

DEHYDROXYFLUORINATION AGENT

TECHNICAL FIELD

The present invention relates to a novel dehydroxyfluorination agent.

BACKGROUND OF THE INVENTION

"Dehydroxyfluorination reaction" for replacing hydroxyl group of a hydroxyl group-containing compound with fluorine atom is an important reaction in syntheses of fluorine-containing organic compounds. The following are typical examples.

1) a process (Patent Publication 1 and Patent Publication 2) in which a substrate having a hydroxyl group is reacted with a perfluoroalkanesulfonyl fluoride, such as perfluorobutanesulfonyl fluoride, in the presence of a special, strongly basic, organic base, such as DBU (1,8-diazabicyclo[5.4.0]undec-7-ene).

2) a process (Non-patent Publication 1) in which a substrate having a hydroxyl group is reacted with perfluorobutanesulfonyl fluoride in the presence of an organic base, such as triethylamine, and "a salt or complex comprising an organic base and hydrogen fluoride" such as triethylamine tris(hydrogen fluoride) complex.

3) a process (Patent Publications 3-6) for producing a fluoro derivative by reacting a specific hydroxy derivative with trifluoromethanesulfonyl fluoride in the presence of an organic base or in the presence of an organic base and "a salt or complex comprising an organic base and hydrogen fluoride" (such as triethylamine tris(hydrogen fluoride) complex).

4) a process (Non-patent Publication 2) in which a hydroxyl group is converted into a fluorosulfate, followed by replacement with a fluorine anion.

Patent Publication 1: U.S. Pat. No. 5,760,255 specification
Patent Publication 2: U.S. Pat. No. 6,248,889 specification
Patent Publication 3: International Publication 2004/089968 Pamphlet (Japanese Patent Application Publication 2004-323518)
Patent Publication 4: Japanese Patent Application Publication 2006-083163
Patent Publication 5: Japanese Patent Application Publication 2005-336151
Patent Publication 6: Japanese Patent Application Publication 2006-008534
Non-patent Publication 1: Organic Letters (US), 2004, Vol. 6, No. 9, p. 1465-1468
Non-patent Publication 2: Tetrahedron Letters (UK), 1996, Vol. 37, No. 1, p. 17-20

SUMMARY OF THE INVENTION

In the processes of Patent Publication 1 and Patent Publication 2, it was necessary to use a long-chain perfluoroalkanesulfonyl fluoride, which is not preferable in large-scale use, and a high-price, special organic base. In the dehydroxyfluorination reaction using a perfluoroalkanesulfonyl fluoride, a perfluoroalkanesulfonic acid is stoichiometrically produced as a by-product in the form of a salt of an organic base. Therefore, waste treatment of the acid was a large problem in conducting the reaction in large scale. In particular, long-chain perfluoroalkanesulfonic acid derivatives having a carbon number of 4 or greater are pointed out to have long-term persistence in environment and toxicity, and therefore their large-scale use is limited (for example, see FARUMASHIA Vol. 40, No. 2, 2004 with respect to perfluorooctanesulfonic acid derivatives).

Also in the process of Non-patent Publication 1, there was a similar problem of using long-chain perfluorobutanesulfonyl fluoride.

On the other hand, the processes of Patent Publications 3-6 are superior processes that are capable of avoiding problems of long-term persistence in environment and toxicity, since they use trifluoromethanesulfonyl fluoride having a carbon number of 1. The industrial production amount of trifluoromethanesulfonyl fluoride is, however, limited, as compared with perfluorobutanesulfonyl fluoride and perfluorooctanesulfonyl fluoride. Therefore, its obtainment in large amount was not necessarily easy.

The process of Non-patent Publication 2 was not a direct fluorination reaction (see Scheme 1), due to its necessity of going through imidazole sulfate in order to convert the hydroxy derivative to the fluorosulfate.

Scheme 1

[Chemical Formula 1]

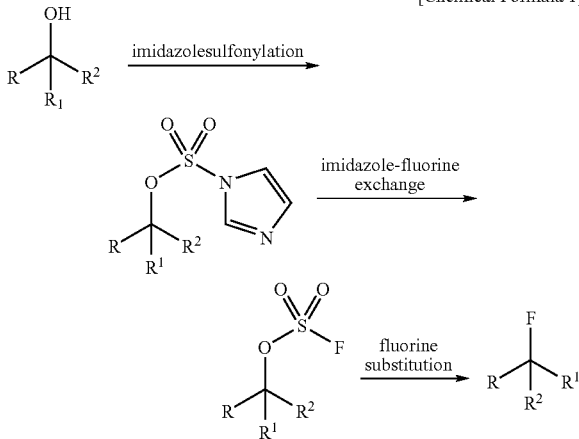

According to Non-patent Publication 1, it is disclosed therein that, when the dehydroxyfluorination agent comprising trifluoromethanesulfonic anhydride, triethylamine tris(hydrogen fluoride) complex and triethylamine is used, gaseous trifluoromethanesulfonyl fluoride (boiling point: −21° C.) is formed in the reaction system, thereby not achieving an efficient trifluoromethanesulfonylation of a hydroxyl group of the substrate, and that a combination with high-boiling-point (64° C.) perfluorobutanesulfonyl fluoride (perfluorobutanesulfonyl fluoride, triethylamine tris(hydrogen fluoride) complex and triethylamine) is preferable. This description clearly indicates that low-boiling-point trifluoromethanesulfonyl fluoride is not preferable as a perfluoroalkanesulfonyl fluoride of the dehydroxyfluorination agent. Sulfuryl fluoride used in the present invention has a further lower boiling point (−49.7° C.). Thus, it has been totally unclear whether or not that can preferably be used as the dehydroxyfluorination agent.

As mentioned hereinbefore, there has been a strong demand for a novel dehydroxyfluorination means that is easy in large-scale operation, for producing fluoro derivatives.

From the above viewpoint, the present inventors have conducted an eager examination to find a novel dehydroxyfluorination means that is easy in large-scale operation. As a result, we have found a novel dehydroxyfluorination agent comprising sulfuryl fluoride ($SO_2F_2$) and an organic base that is free from a free hydroxyl group in the molecule, thereby reaching the present invention.

Sulfuryl fluoride ($SO_2F_2$) is a compound that is widely used as a fumigant. There has been, however, no report of using the compound as a dehydroxyfluorination agent.

By conducting a dehydroxyfluorination using a dehydroxyfluorination agent of the present invention, it is possible to continuously conduct a fluorosulfonylation and a fluorine substitution in one reaction vessel without isolating a fluorosulfate that is a reaction intermediate. As shown in Scheme 2, the characteristic of the present invention is that a hydroxy derivative can be converted into a fluorosulfate by using sulfuryl fluoride and that "a salt or complex comprising an organic base and hydrogen fluoride", which has been stoichiometrically produced as a by-product in the reaction system in the step of this fluorosulfonylation, can be effectively used as a fluorine source of the fluorine substitution.

Furthermore, as shown in Scheme 3, in the case of using "the above dehydroxyfluorination agent further comprising a hydrogen fluoride source (it refers to hydrogen fluoride or a salt or complex formed between hydrogen fluoride and an organic salt) added from the outside of the system", as compared with the process shown in Scheme 2, it was also found that the fluoro derivative can be obtained with high yield and selectivity.

Scheme 2

[Chemical Formula 2]

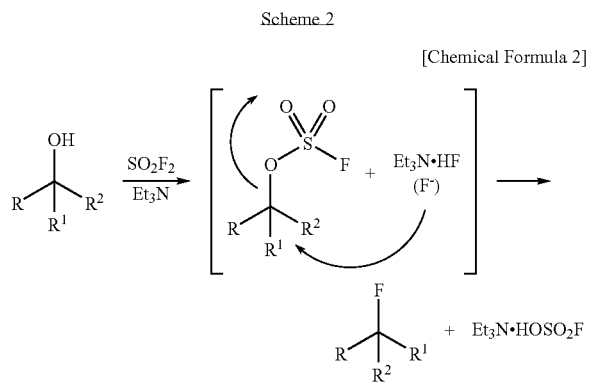

An example in which triethylamine (1 equivalent) has been used as the organic base.

Scheme 3

[Chemical Formula 3]

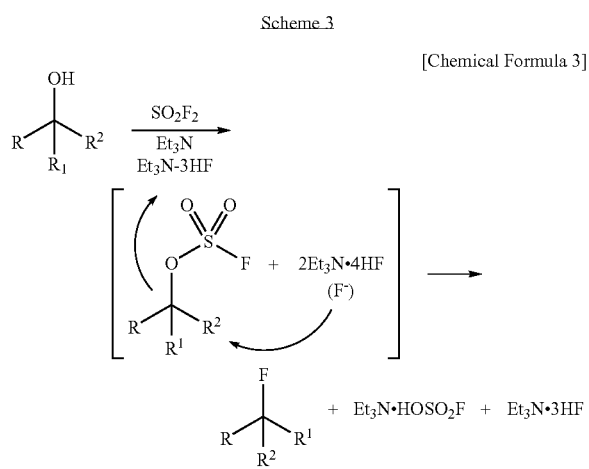

An example in which triethylamine (1 equivalent) has been used as the organic base and in which a triethylamine tris(hydrogen fluoride) complex (1 equivalent) has been used as "the salt or complex comprising an organic base and hydrogen fluoride".

In the present invention, sulfuryl fluoride has two reaction points to the hydroxyl group. However, in the case of using 4-hydroxyproline derivatives, which are particularly optically active hydroxy derivatives, 1-β-D-arabinofuranosyluracil derivatives, optically active α-hydroxycarboxylate derivatives, and primary alcohol derivatives as hydroxy derivatives, it was found that a disubstituted sulfate is almost not given (see Scheme 4) and that the fluorine substitution proceeds well by going through the target fluorosulfate. We have clarified that such problem does not occur by perfluoroalkanesulfonyl fluoride and that sulfuryl fluoride can preferably be used as a dehydroxyfluorination agent.

Scheme 4

[Chemical Formula 4]

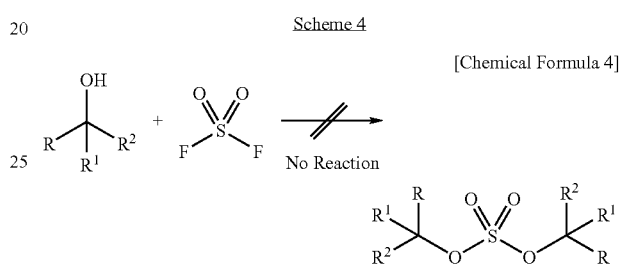

Furthermore, the present inventors have found that stereochemistry of a fluoro derivative obtained by the reaction with sulfuryl fluoride is inverted, in the case of using as the hydroxyl derivative an optically active compound caused by chirality of the carbon atom that is covalently bonded with the hydroxyl group. In the present dehydroxyfluorination reaction, it is considered that the fluorosulfonylation proceeds with maintenance of stereochemistry and the subsequent fluorine substitution proceeds with inversion of stereochemistry. A dehydroxyfluorination reaction accompanied with such inversion of stereochemistry is also already disclosed in a process using a perfluoroalkanesulfonyl fluoride of Patent Publication 2. However, fluorosulfuric acid group is vastly inferior to perfluoroalkanesulfonic acid group in leaving ability [Synthesis (Germany) 1982, Vol. 2, p. 85-126]. Therefore, it was unclear whether or not the reaction proceeds with high asymmetry transcription percentage in a dehydroxyfluorination reaction, using sulfuryl fluoride, of a chain substrate, which is difficult in control of stereochemistry, particularly an optically active α-hydroxycarboxylate derivative. In contrast with this, the present inventors have found that a dehydroxyfluorination using sulfuryl fluoride of the present invention proceeds well under a very mild reaction condition and that an optically active α-fluorocarboxylate derivative, which is extremely high in optical purity, is obtained by the reflection of optical purity of the optically active α-hydroxycarboxylate derivative, which is used as the raw material substrate.

Furthermore, it was unclear whether or not fluorosulfates that are obtained by conversion of 4-hydroxyproline derivative and 1-β-D-arabinofuranosyluracil derivative through fluorosulfonylation and that correspond to the respective raw material substrates have sufficient leaving abilities. In contrast with this too, the present inventors have found that a dehydroxyfluorination reaction using sulfuryl fluoride of the present invention can preferably be used as the process for producing 4-fluoroproline derivative and 2'-deoxy-2'-fluorouridine derivative.

DETAILED DESCRIPTION

Advantageous points of the dehydroxyfluorination agent of the present invention are described in the following, as compared with prior art.

Relative to the processes of Patent Publication 1, Patent Publication 2 and Non-patent Publication 1, it is not necessary to use perfluoroalkanesulfonyl fluorides that are problematic in waste treatment, long-term persistence in environment and toxicity, and it is possible in the present invention to use sulfuryl fluoride, which is widely used as a fumigant.

In the case of conducting a dehydroxyfluorination reaction using a dehydroxyfluorination agent of the present invention, fluorosulfuric acid is stoichiometrically produced as a salt of an organic base. It is, however, possible to easily treat the acid into fluorite ($CaF_2$) as a final waste. It is thus extremely preferable for a fluorination reaction in large scale.

Furthermore, the perfluoroalkyl moiety of perfluoroalkanesulfonyl fluoride is at last not incorporated into the target product. One having a less fluorine content is advantageous in atomic economy, as long as it has sufficient sulfonylation ability and leaving ability. From such a viewpoint too, sulfuryl fluoride is vastly superior.

In a dehydroxyfluorination agent of the present invention, it is not necessary to use a high-price, special organic base such as DBU, and it is possible to use a low-price organic base, such as triethylamine, that is common in large-scale production.

Relative to the process of Non-patent Publication 2, it is not necessary to go through imidazole sulfate. In the present invention, it is possible to directly convert a hydroxy derivative to a fluorosulfate by using sulfuryl fluoride.

Furthermore, a new advantageous effect of the invention has been found by using sulfuryl fluoride. In a dehydroxyfluorination reaction using a perfluoroalkanesulfonyl fluoride, a salt of a perfluoroalkanesulfonic acid and an organic base is stoichiometrically contained in the reaction-terminated liquid. The salt, particularly a salt derived from a perfluoroalkanesulfonic acid having a carbon number of 4 or greater, has an extremely high solubility in organic solvent. We thus have found that there is a problem that it is not possible to effectively remove the salt and thereby it imposes a burden on the purification operation, even if conducting a post-treatment operation that is generally used in organic syntheses, such as washing of organic layer with water or alkali aqueous solution. Furthermore, a salt of perfluoroalkanesulfonic acid and organic base may act as an acid catalyst in some cases. Thus, it was necessary to efficiently remove the salt in order to produce a compound having an acid-labile functional group. Actually, if a large amount of a salt of perfluorobutanesulfonic acid and organic base is contained in a distillation purification of a crude product of 4-fluoroproline derivative, in which the protecting group of the secondary amino group is a tert-butoxycarbonyl (Boc) group, debutoxycarbonylation reaction is found considerably. Thus, it was not possible to recover the target product with good yield. On the other hand, a salt of fluorosulfuric acid and organic base, which is produced as a by-product in the present invention, is extremely high in solubility in water. Therefore, it can perfectly be removed by washing the organic layer with water or alkali aqueous solution. Since it does almost not impose a burden on the purification operation, it was found to be extremely preferable for a fluorination reaction in large scale.

A dehydroxyfluorination agent having characteristics disclosed in the present invention has not been disclosed at all in related technical fields. It is extremely useful as a dehydroxyfluorination agent in large scale, since it is very high in selectivity and does almost not produce as by-products impurities that are difficult in separation. In particular, it can extremely preferably be used for a large-scale production process of optically active fluoro derivatives, which are important intermediates of medicines, agricultural chemicals and optical materials, specifically 4-fluoroproline derivatives, 2'-deoxy-2'-fluorouridine derivatives and optically active α-fluorocarboxylate derivatives, and monofluoromethyl derivatives. It is capable of remarkably efficiently producing them, as compared with conventional production processes.

In the following, a dehydroxyfluorination agent of the present invention is described in more detail.

It is possible to prepare a dehydroxyfluorination agent of the present invention by introducing sulfuryl fluoride into a container in which an organic base exists. In order to further improve reactivity, it is also possible to further add a hydrogen fluoride source (it refers to hydrogen fluoride or a salt or complex formed between hydrogen fluoride and an organic base) from the outside of the system. Furthermore, it is also possible to add an aprotic organic solvent in order to make the reaction proceed more smoothly.

Herein, the container is desirably a pressure-proof airtight container, since sulfuryl fluoride is in gas under ordinary temperature and ordinary pressure.

The order of adding the reagents and the preparation method are not particularly limited. (i) It is possible to prepare a dehydroxyfluorination agent of the present invention by previously placing an organic base that is free from a free hydroxyl group in the molecule (and, according to need, "a hydrogen fluoride source added from the outside of the system" and an aprotic organic solvent) in a container, then sealing it, and introducing gaseous sulfuryl fluoride thereinto. (ii) It is also possible to previously place each component of the above, except sulfuryl fluoride, and the reaction raw material (the hydroxy derivative) into a container and successively or continuously introduce sulfuryl fluoride thereinto. In the case of (ii), the dehydroxyfluorination reaction starts at the same time when the dehydroxyfluorination agent is prepared. Like (ii), to prepare a dehydroxyfluorination agent of the present invention in the reaction system (in situ) is simpler and easier in handling. On the other hand, in large-scale production, it is practical in some cases to introduce sulfuryl fluoride in liquid state under pressurized condition.

The organic base used for a dehydroxyfluorination agent of the present invention is an organic base that is free from a free hydroxyl group in the molecule. In case that a free hydroxyl group exists in a part of the base molecule, it can preferably be used by protecting those hydroxyl groups with various protecting groups. However, as compared with the use by protecting such base, it is economically more preferable to directly use one that is generally available as an organic base with low price. In particular, a base is preferable that is selected from the group consisting of trimethylamine, triethylamine, diisopropylethylamine, tri-n-propylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, and the like. Particularly, triethylamine, diisopropylethylamine, pyridine, 2,4-lutidine, 2,6-lutidine, 3,5-lutidine, and 2,4,6-collidine are preferable.

The present inventors have found that reactivity of the dehydroxyfluorination improves strikingly by further adding "hydrogen fluoride source" to the dehydroxyfluorination agent of the present invention. Herein, "hydrogen fluoride source" refers to hydrogen fluoride or a salt or complex formed between hydrogen fluoride and an organic base.

As shown in Scheme 2, in the dehydroxyfluorination reaction of the present invention, firstly in the fluorosulfate formation, an equimolar amount of hydrogen fluoride (this hydrogen fluoride may form a salt or complex with the organic base) is generated in the system. This hydrogen fluoride becomes a fluorine source in the subsequent fluorine substitution, and it conducts a nucleophilic attack against the fluorosulfate of the reaction intermediate. With this, the fluorine substitution proceeds. This fluorine substitution is markedly accelerated when hydrogen fluoride is in an excessive condition by the addition of the hydrogen fluoride source from the outside of the system. In particular, it was found that a great effect is generated in the case of dehydroxyfluorinating a hydroxy derivative that is low in reactivity.

In a dehydroxyfluorination agent of the present invention, the ratio of sulfuryl fluoride by mol number to the organic base is not particularly limited. However, as shown in Scheme 2, the ratio of sulfuryl fluoride, which is consumed in the dehydroxyfluorination reaction, by mol number to the organic base is 1:1 in theory. Therefore, in principle, it suffices that the ratio of both is about 1:1. However, it is possible in some cases to obtain a higher reactivity by excessively using one of both. Specifically, the ratio of sulfuryl fluoride by mol number to the organic base is preferably in a range of roughly 5:1-1:5.

Furthermore, in the dehydroxyfluorination agent of the present invention, in the case of adding "hydrogen fluoride or a salt or complex formed between hydrogen fluoride and an organic base (e.g., triethylamine tris(hydrogen fluoride) complex)" as a hydrogen fluoride source from the outside of the system, the ratio of sulfuryl fluoride by mol number to the above hydrogen fluoride source (in terms of HF) is preferably in a range of roughly 3:1-1:10, more preferably in a range of 1:1-1:10. If the mol number (in terms of HF) of the hydrogen fluoride source is less than ⅓ of the mol number of sulfuryl fluoride, the effect of positively adding it is low. If it is greater than 10 times that, it becomes disadvantageous in economy and production.

As these organic bases used for "the salt or complex comprising an organic base and hydrogen fluoride" added from the outside of the system, it is possible to preferably use any of the types mentioned as "the organic base that is free from a free hydroxyl group in the molecule", which is an essential element of the present invention. This organic base in the salt or complex may be of a type that is different from the organic base that is an essential element of the present invention, but being the same type is simple. Still triethylamine is one of particularly preferable ones.

In the case of using a salt or complex comprising an organic base and hydrogen fluoride, the molar ratio of the organic base to the hydrogen fluoride in this salt or complex is in a range of 100:1-1:100, preferably in a range of 50:1-1:50 in general, more preferably in a range of 25:1-1:25 in particular. Furthermore, it is extremely convenient to use "a complex comprising 1 mol of triethylamine and 3 mols of hydrogen fluoride" and "a complex comprising ~30% (~10 mol %) of pyridine and ~70% (~90 mol %) of hydrogen fluoride", which are placed on sale from Aldrich (Aldrich, 2003-2004 Comprehensive Catalogue).

Apart from the above-mentioned organic base, it is desirable to further add an aprotic organic solvent in order to have a mutual affinity between sulfuryl fluoride and the organic base in a dehydroxyfluorination agent of the present invention. As such aprotic organic solvent, it is possible to mention aliphatic hydrocarbon series such as n-hexane, cyclohexane and n-heptane; aromatic hydrocarbon series such as benzene, toluene, xylene and mesitylene; halogenated hydrocarbon series such as methylene chloride, chloroform and 1,2-dichloroethane; ether series such as diethyl ether, tetrahydrofuran and tert-butyl methyl ether; ester series such as ethyl acetate and n-butyl acetate; amide series such as N,N-dimethylformamide, N,N-dimethylacetamide and N-methylpyrrolidone; nitrile series such as acetonitrile and propionitrile; dimethylsulfoxide; and the like. Of these, n-heptane, toluene, mesitylene, methylene chloride, tetrahydrofuran, ethyl acetate, N,N-dimethylformamide, N,N-dimethylacetamide, acetonitrile, propionitrile, and dimethylsulfoxide are preferable. In particular, toluene, mesitylene, methylene chloride, tetrahydrofuran, N,N-dimethylformamide, and acetonitrile are more preferable. It is possible to use these reaction solvents alone or in combination.

The amount of the aprotic organic solvent is not particularly limited. It suffices to use 0.1 L (liter) or greater, preferably 0.1-20 L in general, more preferably 0.1-10 L in particular, relative to 1 mole of sulfuryl fluoride.

By using a dehydroxyfluorination agent of the present invention, it is possible to continuously conduct the fluorosulfonylation and the fluorine substitution in one reactor without separation of the fluorosulfate, which is a reaction intermediate.

Furthermore, in the fluorosulfonylation, stereochemistry of the hydroxyl group is maintained, and stereochemistry is inverted in the subsequent fluorine substitution. Therefore, 4-fluoroproline derivative in 4S/2R configuration is obtained from 4-hydroxyproline derivative in 4R/2R configuration. Similarly, 4R/2R configuration from 4S/2R configuration, 4S/2S configuration from 4R/2S configuration, and 4R/2S configuration from 4S/2S configuration. Optically active α-fluorocarboxylate derivative in S configuration at α-position is obtained from optically active α-hydroxycarboxylate derivative in R configuration at α-position. Similarly, R configuration at α-position is obtained from S configuration at α-position with good selectivity.

[Regarding Hydroxy Derivative]

According to a dehydroxyfluorination agent of the present invention, it is possible to substitute F atom for OH group of various hydroxy derivatives (they refer to compounds having at least one free hydroxyl group in the molecule). In the following, a hydroxy derivative, to which a dehydroxyfluorination agent of the present invention can be applied, is described.

As a hydroxy derivative, to which a dehydroxyfluorination agent of the present invention can be applied, it is possible to cite a hydroxy derivative represented by the general formula [1],

[Chemical Formula 5]

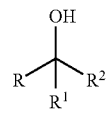

[1]

[in the formula, each of R, $R^1$ and $R^2$ independently represents a hydrogen atom, alkyl group, substituted alkyl group, aromatic ring group, or alkoxycarbonyl group]. By dehydroxyfluorinating the present compound, it is possible to obtain a fluoro derivative represented by the general formula [2],

[Chemical Formula 6]

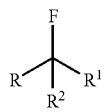

[2]

[in the formula, R, R$^1$ and R$^2$ are defined as in the general formula [1]].

When R, R$^1$ and R$^2$ of the hydroxyl derivative represented by the general formula [1] are alkyl groups, substituted alkyl groups, aromatic ring groups or alkoxycarbonyl groups other than hydrogen atoms, they also can have an optically active moiety caused by chirality of carbon atom, axis and the like. In these cases, stereochemistry of the optically active moiety is maintained through the fluorination reaction of the present invention.

As a hydroxy derivative, to which a dehydroxyfluorination agent of the present invention can be applied, it is possible to cite a hydroxy derivative represented by the general formula [1a],

[Chemical Formula 7]

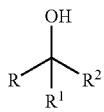

[1a]

[In the formula, each of R, R$^1$ and R$^2$ independently represents a hydrogen atom, alkyl group, substituted alkyl group, aromatic ring group, or alkoxycarbonyl group. The alkyl group is defined as being a C$_1$-C$_{16}$ straight-chain or branched alkyl group. The substituted alkyl group is defined as being an alkyl group, in which a halogen atom, lower alkoxy group, lower haloalkoxy group, lower alkylamino group, lower alkylthio group, cyano group, aminocarbonyl group (CONH$_2$), unsaturated group, aromatic ring group, nucleic acid base, aromatic-ring oxy group, aliphatic heterocyclic group, protected hydroxyl group, protected amino group, protected thiol group, or protected carboxyl group has been substituted therefor by any number and by any combination on any carbon atom of the alkyl group. Any carbon atoms themselves of any two alkyl groups or substituted alkyl groups may form a covalent bond to have an aliphatic ring, and carbon atoms of the aliphatic ring may be partially replaced with nitrogen atom or oxygen atom to have an aliphatic heterocyclic ring. The aromatic ring group is defined as being an aromatic hydrocarbon group or aromatic heterocyclic group containing oxygen atom, nitrogen atom or sulfur atom. The alkoxycarbonyl group is defined as being an alkoxycarbonyl group comprising an C$_1$-C$_{12}$ straight-chain or branched alkoxy group, and any carbon atoms themselves of the alkoxy group and of any alkyl group or substituted alkyl group may form a covalent bond to have a lactone ring.]. By dehydroxyfluorinating the present compound, it is possible to obtain a fluoro derivative represented by the general formula [2a],

[Chemical Formula 8]

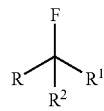

[2a]

[in the formula, R, R$^1$ and R$^2$ are defined as in the general formula [1a]].

The substituted alkyl group of R, R$^1$ and R$^2$ of the hydroxy derivative represented by the general formula [1a] is defined as being "an alkyl group, in which a halogen atom of fluorine, chlorine, bromine and iodine; lower alkoxy group such as methoxy group, ethoxy group and propoxy group; lower haloalkoxy group such as fluoromethoxy group, chloromethoxy group and bromomethoxy group; lower alkylamino group such as dimethylamino group, diethylamino group and dipropylamino group; lower alkylthio group such as methylthio group, ethylthio group and propylthio group; cyano group; aminocarbonyl group (CONH$_2$); unsaturated group such as alkenyl group and alkynyl group; aromatic ring group such as phenyl group and naphthyl group; nucleic acid base such as adenine residue, guanine residue, hypoxanthine residue, xanthine residue, uracil residue, thymine residue and cytosine residue; aromatic-ring oxy group such as phenoxy group and naphthoxy group; aliphatic heterocyclic group such as piperidyl group, piperidino group and morpholyl group; protected hydroxyl group, protected amino group, protected thiol group, protected carboxyl group, or the like has been substituted therefor by any number and by any combination on any carbon atom of the alkyl group".

In the present specification, each of the following terms is used as having the following meaning. "Lower" means C$_1$-C$_6$ straight-chain or branched. In case that "unsaturated group" is a double bond, it can be in a geometrical isomerism of either E configuration or Z configuration. "Aromatic ring group" also can be an aromatic heterocyclic group (containing a condensed skeleton) containing oxygen atom, nitrogen atom, sulfur atom and the like, such as furyl group, pyrrolyl group and thienyl group, other than aromatic hydrocarbon groups. "Nucleic acid base" can be protected with a protecting group that is generally used in the field of syntheses of nucleic acid related substances (For example, as a protecting group of hydroxyl group, it is possible to mention acyl groups such as acetyl group and benzoyl group; alkyl groups such as methoxymethyl group and allyl group; and aralkyl groups such as benzyl group and triphenylmethyl group. As a protecting group of amino group, it is possible to mention acyl groups such as acetyl group and benzoyl group and aralkyl groups such as benzyl group. Furthermore, halogen atom, lower alkyl group, lower alkoxy group and the like can be substituted in these protecting groups.). Furthermore, hydrogen atom, hydroxyl group and amino group of "nucleic acid base" can be replaced with hydrogen atom, amino group, halogen atom, lower alkyl group, lower alkenyl group nitro group and the like. As "protecting groups of hydroxyl group, amino group, thiol group and carboxyl group", it is possible to use protecting groups and the like described in Protective Groups in Organic Synthesis, Third Edition, 1999, John Wiley & Songs, Inc. In "unsaturated group", "aromatic ring group", "aromatic ring oxy group" and "aliphatic heterocyclic group", it is possible to substitute lower alkyl group, halogen atom, lower haloalkyl group, lower alkoxy group, lower haloalkoxy group, lower alkylamino group, lower alkylthio group, cyano group, aminocarbonyl group, protected hydroxyl group, protected amino group, protected thiol group, protected carboxyl group, and the like.

Alkyl group and substituted alkyl group of R, $R^1$ and $R^2$ of the hydroxy derivative represented by the general formula [1a] also can be an aliphatic ring, such as cyclopentane ring and cyclohexane ring, by the formation of a covalent bond by any carbon atoms of any two alkyl groups or substituted alkyl groups. They also can be an aliphatic heterocyclic ring, such as pyrrolidine ring (also containing a protected secondary amino group), piperidine ring (also containing a protected secondary amino group), oxolane ring and oxane ring, in which carbon atoms of the aliphatic ring have been partially replaced with nitrogen atoms or oxygen atoms.

Aromatic ring group of R, $R^1$ and $R^2$ of the hydroxy derivative represented by the general formula [1a] is defined as being "an aromatic hydrocarbon group, such as phenyl group, naphthyl group and anthryl group, or aromatic heterocyclic group containing oxygen atom, nitrogen atom, sulfur atom or the like, such as furyl group, pyrrolyl group, thienyl group, benzofuryl group, indolyl and benzothienyl group. In these aromatic hydrocarbon groups and aromatic heterocyclic groups, it also possible to substitute lower alkyl group, halogen atom, lower haloalkyl group, lower alkoxy group, lower haloalkoxy group, lower alkylamino group, lower alkylthio group, cyano group, aminocarbonyl group, unsaturated group, aromatic ring group, aromatic ring oxy group, aliphatic heterocyclic group, protected hydroxyl group, protected amino group, protected thiol group, protected carboxyl group, and the like.

As a hydroxy derivative, to which a dehydroxyfluorination agent of the present invention can be applied, it is possible to cite an optically active hydroxy derivative represented by the general formula [3],

[Chemical Formula 9]

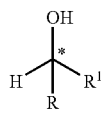

[3]

[In the formula, each of R and $R^1$ is independently an alkyl group, substituted alkyl group, or alkoxycarbonyl group. * represents an asymmetric carbon (R and R' do not take the same substituent). The alkyl group is defined as being a $C_1$-$C_{16}$ straight-chain or branched alkyl group. The substituted alkyl group is defined as being an alkyl group, in which a halogen atom, lower alkoxy group, lower haloalkoxy group, lower alkylamino group, lower alkylthio group, cyano group, aminocarbonyl group ($CONH_2$), unsaturated group, aromatic ring group, nucleic acid base, aromatic-ring oxy group, aliphatic heterocyclic group, protected hydroxyl group, protected amino group, protected thiol group, or protected carboxyl group has been substituted therefor by any number and by any combination on any carbon atom of the alkyl group. Any carbon atoms themselves of two alkyl groups or substituted alkyl groups may form a covalent bond to have an aliphatic ring, and carbon atoms of the aliphatic ring may be partially replaced with nitrogen atom or oxygen atom to have an aliphatic heterocyclic ring. The alkoxycarbonyl group is defined as being an alkoxycarbonyl group comprising an $C_1$-$C_{12}$ straight-chain or branched alkoxy group, and any carbon atoms themselves of the alkoxy group and of any alkyl group or substituted alkyl group may form a covalent bond to have a lactone ring. Stereochemistry of the carbon atom, to which the hydroxyl group is covalently bonded, is inverted through the reaction.] By dehydroxyfluorinating the present compound, it is possible to obtain an optically active fluoro derivative represented by the general formula [4],

[Chemical Formula 10]

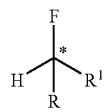

[4]

[In the formula, R, $R^1$ and * are defined as in the general formula [3]].

The dehydroxyfluorination reaction of the present invention becomes particularly effective for the production of high-optical-purity fluoro derivatives, which are required for important intermediates of medicines, agricultural chemicals and optical materials. In order to maximize this effect, the selection of the raw material substrate is important. Specifically, although it can be applied to optically active tertiary alcohol derivatives, which are sterically bulky, optically active secondary alcohol derivatives (corresponding to optically active hydroxy derivatives represented by the general formula [3]), which can be expected to have a high asymmetry transcription percentage, are still more preferable. Furthermore, the substituents of the optically active secondary alcohol derivative (corresponding to R and R' of the optically active hydroxy derivative represented by the general formula [3]) are preferably alkyl group, substituted alkyl group and alkoxycarbonyl group, as compared with aromatic ring groups, which are expected to be accompanied with a partial racemization by going through a transition state, such as the benzyl-position carbonium ion, in the course of the fluorine substitution of the fluorosulfate as the reaction intermediate.

Due to the usefulness of the product to be obtained, the carbon number of the alkyl group is generally preferably 1 to 14, particularly more preferably 1 to 12. The substituents of the substituted alkyl group are preferably nucleic acid base, protected hydroxyl group, protected amino group, and protected carboxyl group. It is preferable that two alkyl groups or substituted alkyl groups take an aliphatic heterocyclic ring. The carbon number of the alkoxy group of the alkoxycarbonyl group is generally preferably 1 to 10, particularly more preferably 1 to 8.

Furthermore, stereochemistry of the asymmetric carbon of the optically active secondary alcohol derivative (corresponding to the optically active hydroxy derivative represented by the general formula [3]) can be R configuration or S configuration. Enantiomer excess ratio (% ee) is not particularly limited. It suffices to use one having 90% ee or greater. In general, 95% ee or greater is preferable, and particularly 97% ee is more preferable.

As a hydroxy derivative, to which a dehydroxyfluorination agent of the present invention can be applied, it is possible to cite a 4-hydroxyproline derivative represented by the general formula [5],

[Chemical Formula 11]

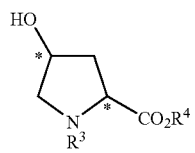

[5]

[In the formula, $R^3$ represents a protecting group of the secondary amino group, $R^4$ represents a protecting group of the carboxyl group, * represents an asymmetric carbon, and stereochemistry of the 4-position is inverted through the reaction, and stereochemistry of the 2-position is maintained.] By dehydroxyfluorinating the present compound, it is possible to obtain a 4-fluoroproline derivative represented by the general formula [6],

[Chemical Formula 12]

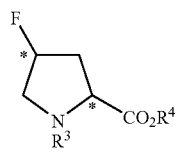

[6]

[In the formula, $R^3$, $R^4$ and * are defined as in the general formula [5]].

As the protecting group $R^3$ of the secondary amino group of the 4-hydroxyproline derivative represented by the general formula [5], it is possible to mention benzyloxycarbonyl (Z) group, tert-butoxycarbonyl (Boc) group, 9-fluorenylmethoxycarbonyl (Fmoc) group, 3-nitro-2-pyridinesulfenyl (Npys) group, p-methoxybenzyloxycarbonyl [Z(MeO)] group, and the like. Of these, benzyloxycarbonyl (Z) group and tert-butoxycarbonyl (Boc) group are preferable, and particularly tert-butoxycarbonyl (Boc) group is more preferable.

As the protecting group $R^4$ of the carboxyl group of the 4-hydroxyproline derivative represented by the general formula [5], it is possible to mention methyl (Me) group, ethyl (Et) group, tert-butyl (t-Bu) group, trichloroethyl (Tce) group, phenacyl (Pac) group, benzyl (Bzl) group, 4-nitrobenzyl [Bzl(4-$NO_2$)] group, 4-methoxybenzyl [Bzl(4-MeO)] group, and the like. Of these, methyl (Me) group, ethyl (Et) group and benzyl (Bzl) group are preferable, and particularly methyl (Me) group and ethyl (Et) group are more preferable.

It is possible to produce the 4-hydroxyproline derivative represented by the general formula [5] from a commercial optically active 4-hydroxyproline by referring to 4th Edition Jikken Kagaku Koza 22 Organic Synthesis IV Acid, Amino acid, Peptide (Maruzen, 1992, p. 193-309). Depending on a combination of the protecting group $R^3$ of the secondary amino group and the protecting group $R^4$ of the carboxyl group, there are commercial products, and it is also possible to use these. Of the 4-hydroxyproline derivative represented by the general formula [5], it is possible to easily convert a hydrochloride of optically active 4-hydroxyproline methyl ester into one in which the protecting group $R^3$ of the secondary amino group is a tert-butoxycarbonyl (Boc) group and in which the protecting group $R^4$ of the carboxyl group is a methyl (Me) group, in accordance with Tetrahedron Letters (United Kingdom), 1988, Vol. 39, No. 10, p. 1169-1172.

As stereochemistry of the asymmetric carbon of the 4-hydroxyproline derivative represented by the general formula [5], each of 2-position and 4-position can independently take R configuration or S configuration. As a combination of stereochemistry, there is 4R/2R form, 4S/2R form, 4R/2S form or 4S/2S form. Enantiomer excess ratio (% ee) or diastereomer excess ratio (% de) of each stereoisomer is not particularly limited. It suffices to use 90% ee or 90% de or greater, normally preferably 95% ee or 95% de or greater, particularly more preferably 97% ee or 97% de or greater.

As a hydroxy derivative, to which a dehydroxyfluorination agent of the present invention can be applied, it is possible to cite a 1-β-D-arabinofuranosyluracil derivative represented by the general formula [7],

[Chemical Formula 13]

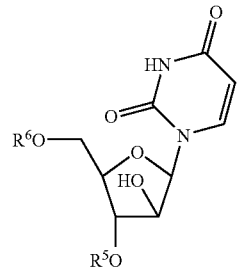

[7]

[In the formula, each of $R^5$ and $R^6$ independently represents a protecting group of the hydroxyl group.]. By dehydroxyfluorinating the present compound, it is possible to obtain a 2'-deoxy-2'-fluorouridine derivative represented by the general formula [8],

[Chemical Formula 14]

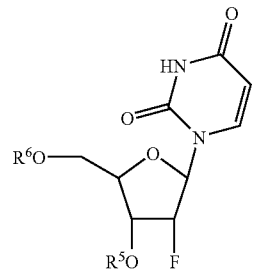

[8]

[In the formula, $R^5$ and $R^3$ are defined as in the general formula [7].].

As the protecting groups $R^5$ and $R^6$ of the hydroxyl groups of the 1-β-D-arabinofuranosyluracil derivative represented by the general formula [7], it is possible to mention trithyl group (triphenylmethyl group), tetrahydropyranil group (THP group), and tetrahydrofuranyl group (THF group). Of these, tetrahydropyranil group (THP group), and tetrahydrofuranyl group (THF group) are preferable, and particularly tetrahydropyranil group (THP group) is more preferable. It is possible to produce 1-β-D-arabinofuranosyluracil derivative represented by the general formula [7] by referring to Chem. Pharm. Bull. (Japan), 1994, Vol. 42, No. 3, p. 595-598 and Khim. Geterotsikl. Soedin. (Russia), 1996, No. 7, p. 975-977. It is possible to obtain one, in which hydroxyl groups of 3'-position and 5'-position are selectively protected, by following the processes of these publications.

As a hydroxy derivative, to which a dehydroxyfluorination agent of the present invention can be applied, it is possible to cite an optically-active, α-hydroxycarboxylate derivative represented by the general formula [9],

[Chemical Formula 15]

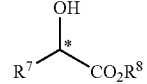

[9]

[In the formula, $R^7$ represents a $C_1$-$C_{12}$ alkyl group or substituted alkyl group, $R^8$ represents a $C_1$-$C_8$ alkyl group, any carbon atoms themselves of the alkyl group or of the substituted alkyl group of $R^7$ and $R^8$ may form a covalent bond to have a lactone ring, * represents an asymmetric carbon, and stereochemistry of the α-position is inverted through the reaction.]. By dehydroxyfluorinating the present compound, it is possible to obtain an optically-active, α-fluorocarboxylate derivative represented by the general formula [10],

[Chemical Formula 16]

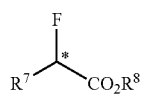

[10]

[In the formula, $R^7$, $R^8$ and * are defined as in the general formula [9].].

As $R^7$ of the optically active α-hydroxycarboxylate derivative represented by the general formula [9], it is possible to mention methyl group, ethyl group, propyl group, butyl group, amyl group, hexyl group, heptyl group, octyl group, nonyl group, decyl group, undecyl group, and lauryl group. The alkyl group having a carbon number of 3 or greater can be straight-chain or branched. On any carbon atom of the alkyl group, it is possible to substitute one or any combination of two of aromatic hydrocarbon groups such as phenyl group and naphthyl group, unsaturated hydrocarbon groups such as vinyl group, $C_1$-$C_6$ straight-chain or branched alkoxy groups, aryloxy groups such as phenoxy group, halogen atoms (fluorine, chlorine, bromine and iodine), protected carboxyl groups, protected amino groups, or protected hydroxyl groups. As the protecting groups of the carboxyl group, amino group and hydroxyl group, similar to the above, it is possible to use protecting groups described in Protective Groups in Organic Synthesis, Third Edition, 1999, John Wiley & Sons, Inc. Specifically, it is possible to mention ester group and the like as the protecting group of the carboxyl group. It is possible to mention benzyl group, acyl groups (acetyl group, chloroacetyl group, benzoyl group, 4-methylbenzoyl group and the like), and phthaloyl group, and the like as the protecting group of the amino group. It is possible to mention benzyl group, 2-tetrapyranil group, acyl groups (acetyl group, chloroacetyl group, benzoyl group, 4-methylbenzoyl group and the like), silyl groups (trialkylsilyl group, alkylarylsilyl group and the like), and the like, as the protecting group of the hydroxyl group. In particular, it is possible to mention a protecting group or the like that forms 2,2-dimethyl-1,3-dioxolane, as the protecting group of the 1,2-dihydroxy group.

Although the production process, which is the target of the present invention, can be used even in case that $R^7$ of the optically active α-hydroxycarboxylate derivative represented by the general formula [9] is an aromatic hydrocarbon group, optical purity of the target product, optically active α-fluorocarboxylate derivative ($R^7$=an aromatic hydrocarbon group) represented by the general formula [10], lowers significantly, as compared with a case that $R^7$ is an alkyl group or substituted alkyl group. Therefore, an alkyl group or substituted alkyl group is preferable as $R^7$ of the optically active α-hydroxycarboxylate derivative represented by the general formula [9].

As $R^8$ of the optically active α-hydroxycarboxylate derivative represented by the general formula [9], it is possible to mention methyl group, ethyl group, propyl group, butyl group, amyl group, hexyl group, heptyl group, and octyl group. The alkyl group having a carbon number of 3 or greater can be straight-chain or branched.

Stereochemistry of the asymmetric carbon of the optically active α-hydroxycarboxylate derivative represented by the general formula [9] can be R configuration or S configuration. Enantiomer excess ratio (% ee) is not particularly limited. It suffices to use one having 90% ee or greater. In general, 95% ee or greater is preferable, and particularly 97% ee is more preferable.

The optically active α-hydroxycarboxylate derivative represented by the general formula [9] can be produced similarly from various, commercial, optically-active, α-amino acids by referring to Synthetic Communications (US), 1991, Vol. 21, No. 21, p. 2165-2170. A commercial product was used as (S)-ethyl lactate used in the Examples.

As a hydroxy derivative, to which a dehydroxyfluorination agent of the present invention can be applied, it is possible to cite a primary alcohol derivative represented by the general formula [11],

[Chemical Formula 17]

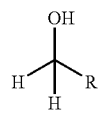

[11]

[In the formula, R represents an alkyl group or substituted alkyl group, the alkyl group is defined as being a $C_1$-$C_{16}$ straight-chain or branched alkyl group, and the substituted alkyl group is defined as being an alkyl group, in which a halogen atom, lower alkoxy group, lower haloalkoxy group, lower alkylamino group, lower alkylthio group, cyano group, aminocarbonyl group ($CONH_2$), unsaturated group, aromatic ring group, nucleic acid base, aromatic-ring oxy group, aliphatic heterocyclic group, protected hydroxyl group, protected amino group, protected thiol group, or protected carboxyl group has been substituted therefor by any number and by any combination on any carbon atom of the alkyl group.]. By dehydroxyfluorinating the present compound, it is possible to obtain a monofluoromethyl derivative represented by the general formula [12],

[Chemical Formula 18]

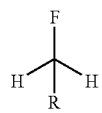

[12]

[In the formula, R is defined as in the general formula [11].].

In the development of medicines having new effectiveness, "monofluoromethyl group" is recognized as being an important motif. Thus, primary alcohol derivatives (corresponding to the primary alcohol derivative represented by the general formula [11]), which can efficiently produce monofluoromethyl derivatives (corresponding to the monofluoromethyl derivative represented by the general formula [12]), are also preferable substrates.

The optically active hydroxy derivative represented by the general formula [3], the 4-hydroxyproline derivative represented by the general formula [5], 1-β-D-arabinofuranosyluracil derivative represented by the general formula [7], the optically active α-hydroxycarboxylate derivative represented by the general formula [9], and the primary alcohol derivative represented by the general formula [11] are particularly preferable as the hydroxy derivative represented by the general formula [1].

[Reaction Conditions of Dehydroxyfluorination]

The amount of sulfuryl fluoride ($SO_2F_2$) used in the dehydroxyfluorination agent of the present invention relative to 1 mol of the hydroxy derivative is not particularly limited. It suffices to use 1 mol or greater, preferably 1-10 moles in general, and more preferably 1-5 moles in particular.

The amount of the organic base used in the dehydroxyfluorination of the present invention relative to 1 mol of the hydroxy derivative is not particularly limited. It suffices to use 1 mol or greater, preferably 1-20 moles in general, more preferably 1-10 moles in particular.

The amount of the hydrogen fluoride source (it refers to hydrogen fluoride or a salt or complex formed between hydrogen fluoride and organic base) used in the dehydroxyfluorination agent of the present invention relative to 1 mol of the hydroxy derivative is not particularly limited. It suffices to use 0.3 moles or greater, preferably 0.5-50 moles in general, more preferably 0.7-25 moles in particular.

The temperature condition of the dehydroxyfluorination of the present invention is not particularly limited. It suffices to conduct it in a range of −100 to +100° C., preferably −80 to +80° C. in general, more preferably −60 to +60° C. in particular. In the case of conducting the reaction under a temperature condition that is not lower than boiling point (−49.7° C.) of sulfuryl fluoride, it is possible to use a pressure-proof reaction vessel.

The pressure condition of the dehydroxyfluorination of the present invention is not particularly limited. It suffices to conduct it in a range of atmospheric pressure to 2 MPa, preferably atmospheric pressure to 1.5 MPa in general, more preferably atmospheric pressure to 1 MPa in particular. Therefore, it is preferable to conduct the reaction using a pressure-proof reaction vessel made of a material such as stainless steel (SUS) or glass (glass lining).

The reaction time of the dehydroxyfluorination of the present invention is not particularly limited. It suffices to conduct it in a range of 0.1 to 72 hours. Since it depends on substrate and the reaction conditions, it is preferable to determine the time, at which the raw material has almost disappeared, as the end point, while tracing the progress of the reaction by an analytical means such as gas chromatography, liquid chromatography, or NMR.

The post-treatment of the dehydroxyfluorination of the present invention is not particularly limited. Normally, it is possible to obtain a crude product by pouring the reaction-terminated liquid into water or an aqueous solution of inorganic base (for example, sodium hydrogencarbonate, potassium hydrogencarbonate, sodium carbonate or potassium carbonate) of alkali metal, followed by extraction with an organic solvent (for example, toluene, mesitylene, methylene chloride or ethyl acetate). A salt formed of fluorosulfuric acid and organic base or an alkali metal salt of fluorosulfuric acid, which is produced as a by-product from sulfuryl fluoride, is remarkably high in distribution to water. Therefore, it is possible to efficiently remove these salts by an easy operation such as washing with water and to obtain the target fluoro derivative with high chemical purity. According to need, it can be purified to have a higher chemical purity by activated carbon treatment, distillation, recrystallization and the like.

EXAMPLES

In the following, embodiments of the present invention are specifically explained by examples. The present invention is, however, not limited to these examples.

Example 1

A pressure-proof reaction vessel made of stainless steel (SUS) was charged with 2.45 g (9.99 mmol, 1.00 eq) of 4-hydroxyproline derivative represented by the following formula,

[Chemical Formula 19]

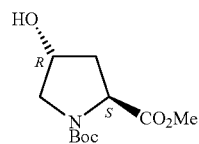

10.0 mL of acetonitrile, and 1.10 g (10.87 mmol, 1.09 eq) of triethylamine, followed by lowering the inside temperature to −40° C. and then bubbling 2.00 g (19.60 mmol, 1.96 eq) of sulfuryl fluoride from a cylinder. The inside temperature was returned to room temperature, and stirring was conducted for 20 hours and 20 minutes. Conversion of the reaction was found by gas chromatography measurement to be 100%. The reaction-terminated liquid was poured into a potassium carbonate aqueous solution [prepared from 2.80 g (20.26 mmol, 2.03 eq) of potassium carbonate and 50.0 mL of water], followed by extraction two times with 50.0 mL of ethyl acetate. The recovered organic layer was concentrated under reduced pressure, followed by vacuum drying, thereby obtaining a crude product of 4-fluoroproline derivative represented by the following formula,

[Chemical Formula 20]

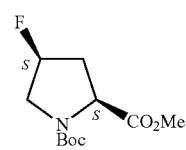

as a brown-color, oil-like substance. The recovered amount of the crude product was slightly greater than the weight of the theoretical yield. Selectivity of the crude product was found by gas chromatography measurement to be 82.4% (As major three kinds of impurities were named Impurities A-C, Impurity A, Impurity B and Impurity C were respectively contained by 8.2%, 3.3% and 4.9%.) Instrument data of the crude product of the obtained 4-fluoroproline derivative are shown in the following (assigned as a mixture of E/Z isomers resulting from the NBoc group). It was found by $^{19}$F-NMR spectrum that the crude product did not contain at all a salt ($FSO_3H\cdot Et_3N$ or $FSO_3K$) derived from fluorosulfuric acid.

$^1$H-NMR (standard substance: $Me_4Si$, heavy solvent: $CDCl_3$), δppm: 1.43&1.49 (s×2, total 9H), 1.95-2.55 (total 2H), 3.51-3.94 (total 2H), 3.75 (S, 3H), 4.36-4.58 (total 1H), 5.10-5.31 (total 1H).

$^{19}$F-NMR (standard substance: $C_6F_6$, heavy solvent: $CDCl_3$), δppm: −11.27 (total 1F).

Example 2

A pressure-proof reaction vessel made of stainless steel (SUS) was charged with 2.45 g (9.99 mmol, 1.00 eq) of 4-hydroxyproline derivative represented by the following formula,

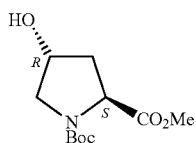
[Chemical Formula 21]

13.0 mL of acetonitrile, 3.50 g (34.59 mmol, 3.46 eq) of triethylamine, and 1.60 g (9.92 mmol, 0.99 eq) of triethylamine tris(hydrogen fluoride) complex, followed by lowering the inside temperature to −40° C. and then bubbling 2.00 g (19.60 mmol, 1.96 eq) of sulfuryl fluoride from a cylinder. The inside temperature was returned to room temperature, and stirring was conducted for 20 hours. Conversion of the reaction was found by gas chromatography measurement to be 100%. The reaction-terminated liquid was poured into a potassium carbonate aqueous solution [prepared from 6.30 g (45.58 mmol, 4.56 eq) of potassium carbonate and 100.0 mL of water], followed by extraction two times with 100.0 mL of ethyl acetate. The recovered organic layer was concentrated under reduced pressure, followed by vacuum drying, thereby obtaining a crude product of 4-fluoroproline derivative represented by the following formula,

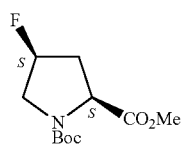
[Chemical Formula 22]

as a brown-color, oil-like substance. The recovered amount of the crude product was slightly greater than the weight of the theoretical yield. Selectivity of the crude product was found by gas chromatography measurement to be 91.0% (As major three kinds of impurities were named Impurities A-C, Impurity A, Impurity B and Impurity C were respectively contained by 6.4%, 2.4% and 0.1%.) Instrument data of the crude product of the obtained 4-fluoroproline derivative were similar to those of Example 1.

Example 3

A pressure-proof reaction vessel made of stainless steel (SUS) was charged with 12.30 g (29.82 mmol, 1.00 eq) of 1-β-D-arabinofuranosyluracil derivative represented by the following formula,

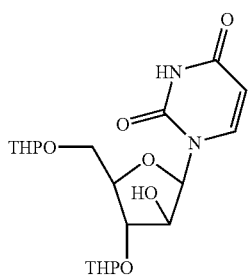
[Chemical Formula 23]

38.0 mL of acetonitrile, 18.15 g (179.37 mmol, 6.02 eq) of triethylamine, and 19.30 g (119.71 mmol, 4.01 eq) of triethylamine tris(hydrogen fluoride) complex, followed by lowering the inside temperature to −40° C. and then bubbling 10.00 g (97.98 mmol, 3.29 eq) of sulfuryl fluoride from a cylinder. The inside temperature was returned to room temperature, and stirring was conducted for 16 hours and 30 minutes and then at 40° C. for 5 hours and 30 minutes. Conversion of the reaction was found by liquid chromatography measurement to be not lower than 99%. The reaction-terminated liquid was poured into a potassium carbonate aqueous solution [prepared from 58.00 g (419.65 mmol, 14.07 eq) of potassium carbonate and 300.0 mL of water], followed by extraction two times with 300.0 mL of ethyl acetate. The recovered organic layer was washed with 200.0 mL of 10% brine, followed by concentration under reduced pressure and vacuum drying, thereby obtaining 12.83 g of a crude product of 2'-deoxy-2'-fluorouridine derivative represented by the following formula,

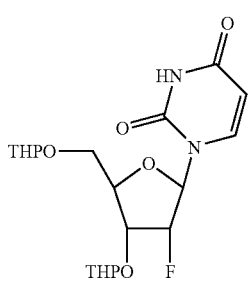
[Chemical Formula 24]

as a brown-color, oil-like substance. The recovered amount of the crude product was slightly greater than the weight of the theoretical yield. Selectivity of the crude product was found by liquid chromatography measurement to be 83.2%. Instrument data of the crude product of the obtained 2'-deoxy-2'-fluorouridine derivative are shown in the following (four kinds of diastereomers resulting from two THP groups were observed).

$^{19}$F-NMR (standard substance: $C_6F_6$, heavy solvent: $CDCl_3$), δppm: −43.13 (dt, 51.9 Hz, 15.4 Hz), −42.50 (dt, 51.5 Hz, 15.4 Hz), −37.62 (dt, 51.5 Hz, 15.0 Hz), −37.55 (dt, 51.9 Hz, 15.0 Hz)/total 1F.

Example 4

A pressure-proof reaction vessel made of stainless steel (SUS) was charged with 9.60 g (81.27 mmol, 1.00 eq, optical purity: 98.4% ee) of an optically-active, α-hydroxycarboxylate derivative represented by the following formula,

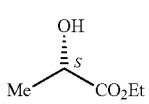
[Chemical Formula 25]

27.0 mL of mesitylene, and 8.50 g (84.00 mmol, 1.03 eq) of triethylamine, followed by lowering the inside temperature to −40° C. and then bubbling 11.50 g (112.68 mmol, 1.39 eq) of sulfuryl fluoride from a cylinder. The inside temperature was returned to room temperature, and stirring was conducted for 22 hours and 10 minutes. Conversion of the reaction was found by gas chromatography measurement to be 100%. The reaction-terminated liquid was poured into a potassium carbonate aqueous solution [prepared from 7.90 g (57.16 mmol, 0.70 eq) of potassium carbonate and 100.0 mL of water], followed by extraction two times with 45.0 mL of mesitylene. The recovered organic layer was washed with a hydrochloric acid brine (prepared from 95.0 mL of 1N hydrochloric acid and 10.00 g of common salt), thereby obtaining 110.63 g of a mesitylene solution of a crude product of an optically-active, α-fluorocarboxylate derivative represented by the following formula.

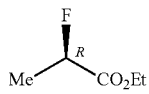

[Chemical Formula 26]

Selectivity of the crude product was found by gas chromatography measurement to be not less than 99.0% (except mesitylene). The mesitylene solution of the crude product was subjected to a fractional distillation (81-90° C./20000 Pa), thereby recovering 26.82 g of a main fraction. The main fraction was found by $^1$H-NMR spectrum to contain 46.90 mmol of the optically-active, α-fluorocarboxylate derivative, and the main fraction concentration was 21.0 wt %. The total yield was 58%. Optical purity and instrument data of the main fraction of the obtained optically-active, α-fluorocarboxylate derivative are shown in the following.

Optical purity: 97.7% ee (It was determined by conducting a hydride reduction using excessive aluminum lithium hydride in tetrahydrofuran, then by leading the obtained (R)-2-fluoro-1-propanol into Mosher ester, and then by conducting gas chromatography. Asymmetry transcription percentage was 99.3%.)

$^1$H-NMR (standard substance: Me$_4$Si, heavy solvent: CDCl$_3$), δppm: 1.32 (t, 7.2 Hz, 3H), 1.58 (dd, 23.6 Hz, 6.9 Hz, 3H), 4.26 (q, 7.2 Hz, 2H), 5.00 (dq, 49.0 Hz, 6.9 Hz, 1H).

$^{19}$F-NMR (standard substance: C$_6$F$_6$, heavy solvent: CDCl$_3$), δppm: −21.88 (dq, 48.9 Hz, 24.4 Hz, 1F)

Example 5

A pressure-proof reaction vessel made of stainless steel (SUS) was charged with 3.50 g (15.00 mmol, 1.00 eq) of a primary alcohol derivative represented by the following formula,

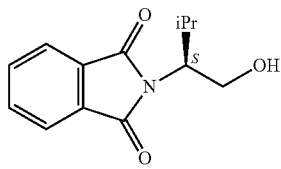

[Chemical Formula 27]

30.0 mL of acetonitrile, 8.35 g (82.52 mmol, 5.50 eq) of triethylamine, and 4.84 g (30.02 mmol, 2.00 eq) of triethylamine tris(hydrogen fluoride) complex, followed by lowering the inside temperature to −40° C. and then bubbling 7.86 g (77.01 mmol, 5.13 eq) of sulfuryl fluoride from a cylinder. The inside temperature was returned to room temperature, and stirring was conducted for 1 hr and 10 minutes. Stirring was further conducted at 60° C. for 39 hours and 30 minutes. Conversion of the reaction was found by gas chromatography measurement to be 100%. 50.0 mL of water were added to the reaction-terminated liquid, followed by concentration under reduced pressure, then adding 50.0 mL of water to the concentrated residue, and then conducting an extraction one time with 100.0 mL of ethyl acetate. The recovered organic layer was dried with anhydrous sodium sulfate, followed by concentration under reduced pressure and vacuum drying, thereby obtaining 2.72 g of a crude product of a monofluoromethyl derivative represented by the following formula,

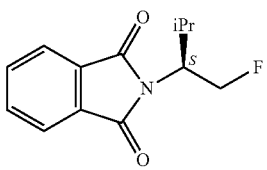

[Chemical Formula 28]

as a dark brown color, oil-like substance. Selectivity of the crude product was found by gas chromatography measurement to be 69.4%. The crude product was found by internal standard method (internal standard substance: C$_6$F$_6$) of $^{19}$F-NMR to contain 3.45 mmol of the monofluoromethyl derivative. The yield was 23%. Instrument data of the crude product of the obtained monofluoromethyl derivative are shown in the following.

$^1$H-NMR (standard substance: Me$_4$Si, heavy solvent: CDCl$_3$), δppm: 0.90 (d, 6.8 Hz, 3H), 1.08 (d, 6.8 Hz, 3H), 2.44 (m, 1H), 4.24 (m, 1H), 4.76 (ddd, 46.6 Hz, 9.5 Hz, 4.8 Hz, 1H), 5.01 (dt, 46.6 Hz, 9.5 Hz, 1H), 7.74 (Ar—H, 2H), 7.86 (Ar—H, 2H).

$^{19}$F-NMR (standard substance: C$_6$F$_6$, heavy solvent: CDCl$_3$), δppm: −62.12 (dt, 13.3 Hz, 46.6 Hz, 1F).

It is possible to produce the primary alcohol derivative of the raw material substrate from a commercial optically active valinol by referring to Protective Groups in Organic Synthesis, Third Edition, 1999, John Wiley & Sons, Inc. The obtained monofluoromethyl derivative can be converted to optically active 1-isopropyl-2-fluoroethylamine without damaging optical purity by referring to the same book.

Example 6

A pressure-proof reaction vessel made of stainless steel (SUS) was charged with 1.39 g (7.98 mmol, 1.00 eq) of a primary alcohol derivative represented by the following formula,

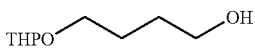

[Chemical Formula 29]

16.0 mL of acetonitrile, 4.45 g (43.98 mmol, 5.51 eq) of triethylamine, and 2.58 g (16.00 mmol, 2.01 eq) of triethylamine tris(hydrogen fluoride) complex, followed by lowering the inside temperature to −40° C. and then bubbling 3.00 g (29.39 mmol, 3.68 eq) of sulfuryl fluoride from a cylinder. The inside temperature was returned to room temperature, and stirring was conducted for 19 hr and 15 minutes. Conversion of the reaction was found by gas chromatography measurement to be 100%. 10.0 mL of water were added to the reaction-terminated liquid, followed by concentrating acetonitrile under reduced pressure and then conducting an extraction of the concentrated residue one time with 30.0 mL of ethyl acetate. The recovered organic layer was washed with 10.0 mL of saturated brine, followed by drying with anhydrous sodium sulfate, concentration under reduced pressure and vacuum drying, thereby obtaining 0.36 g of a crude product of a monofluoromethyl derivative represented by the following formula,

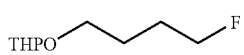
[Chemical Formula 30]

as a brown color, oil-like substance. Selectivity of the crude product was found by gas chromatography measurement to be 98.6%. The yield was 26%. Instrument data of the crude product of the obtained monofluoromethyl derivative are shown in the following.

$^1$H-NMR (standard substance: Me$_4$Si, heavy solvent: CDCl$_3$), δppm: 1.42-1.88 (m, 10H), 3.35-3.52 (m, 2H), 3.70-3.88 (m, 2H), 4.45 (dt, 46.8 Hz, 6.1 Hz, 2H), 4.56 (m, 1H).

$^{19}$F-NMR (standard substance: C$_6$F$_6$, heavy solvent: CDCl$_3$), δppm: −56.37 (septet, 23.4 Hz, 1F).

It is possible to produce the primary alcohol derivative of the raw material substrate from a commercial optically active 1,4-butanediol by referring to Protective Groups in Organic Synthesis, Third Edition, 1999, John Wiley & Sons, Inc. The obtained monofluoromethyl derivative can be converted to 4-fluoro-1-butanol by referring to the same book.

Example 7

A pressure-proof reaction vessel made of stainless steel (SUS) was charged with 1.58 g (9.98 mmol, 1.00 eq) of a primary alcohol derivative represented by the following formula,

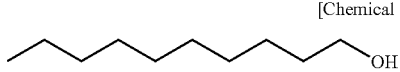
[Chemical Formula 31]

20.0 mL of acetonitrile, 5.57 g (55.04 mmol, 5.52 eq) of triethylamine, and 3.22 g (19.97 mmol, 2.00 eq) of triethylamine tris(hydrogen fluoride) complex, followed by lowering the inside temperature to −40° C. and then bubbling 2.04 g (19.99 mmol, 2.00 eq) of sulfuryl fluoride from a cylinder. The inside temperature was returned to room temperature, and stirring was conducted for 22 hr and 20 minutes. Conversion of the reaction was found by gas chromatography measurement to be 100%. 20.0 mL of water were added to the reaction-terminated liquid, followed by conducting an extraction one time with 20.0 mL of ethyl acetate. The recovered organic layer was washed with 20.0 mL of water and then with 20.0 mL of saturated brine, followed by drying with anhydrous sodium sulfate and concentration under reduced pressure, thereby obtaining a crude product of a monofluoromethyl derivative represented by the following formula,

[Chemical Formula 32]

as a brown color, oil-like substance. Selectivity of the crude product was found by gas chromatography measurement to be 94.2%. The crude product was found by internal standard method (internal standard substance: C$_6$F$_6$) of $^{19}$F-NMR to contain 2.10 mmol of the monofluoromethyl derivative. The yield was 21%. Instrument data of the crude product of the obtained monofluoromethyl derivative are shown in the following.

$^1$H-NMR (standard substance: Me$_4$Si, heavy solvent: CDCl$_3$), δppm: 0.89 (t, 6.8 Hz, 3H), 1.20-1.45 (m, 14H), 1.60-1.70 (m, 2H), 4.44 (dt, 47.6 Hz, 6.2 Hz, 2H).

$^{19}$F-NMR (standard substance: C$_6$F$_6$, heavy solvent: CDCl$_3$), δppm: −55.97 (septet, 23.8 Hz, 1F).

A commercial product was used as the primary alcohol derivative of the raw material substrate.

The invention claimed is:

1. A dehydroxyfluorination agent consisting essentially of:
   sulfuryl fluoride (SO$_2$F$_2$);
   an organic base that is free from a free hydroxyl group in the molecule; and
   an aprotic organic solvent.

2. A dehydroxyfluorination agent according to claim 1, wherein the aprotic organic solvent is at least one selected from the group consisting of n-heptane, toluene, mesitylene, methylene chloride, tetrahydrofuran, ethyl acetate, N,N-dimethylformamide, N,N-dimethylacetamide, acetonitrile, propionitrile, and dimethylsulfoxide.

3. A dehydroxyfluorination agent according to claim 1, wherein the aprotic organic solvent is at least one selected from the group consisting of toluene, mesitylene, methylene chloride, tetrahydrofuran, N,N-diemethylformamide, and acetonitrile.

4. A dehydroxyfluorination agent consisting essentially of:
   sulfuryl fluoride (SO$_2$F$_2$); and
   an organic base that is free from a free hydroxyl group in the molecule.

5. A dehydroxyfluorination agent according to claim 4, wherein a ratio of the sulfuryl fluoride by mol number to the organic base is in a range of 1:5 to 5:1.

6. A dehydroxyfluorination agent according to claim 4, further consisting essentially of a hydrogen fluoride source added from outside of system, the hydrogen fluoride source being defined as hydrogen fluoride or a salt or complex formed between hydrogen fluoride and an organic base.

7. A dehydroxyfluorination agent according to claim 6, wherein a ratio of the sulfuryl fluoride by mol number to the hydrogen fluoride source, in terms of HF, added from the outside of the system is in a range of 1:10 to 3:1.

8. A dehydroxyfluorination agent according to claim 4, wherein the organic base is selected from the group consisting of trimethylamine, triethylamine, diisopropylethylamine, tri-n-propylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, and 3,5,6-collidine.

* * * * *